(12) United States Patent
Koslow

(10) Patent No.: US 6,866,704 B2
(45) Date of Patent: *Mar. 15, 2005

(54) MICROPOROUS FILTER MEDIA WITH INTRINSIC SAFETY FEATURE

(75) Inventor: Evan E. Koslow, Weston, CT (US)

(73) Assignee: Koslow Technologies Corporation, Orange, CT (US)

(*) Notice: Subject to any disclaimer, the term of this patent is extended or adjusted under 35 U.S.C. 154(b) by 17 days.

This patent is subject to a terminal disclaimer.

(21) Appl. No.: 10/412,499

(22) Filed: Apr. 11, 2003

(65) Prior Publication Data

US 2003/0200868 A1 Oct. 30, 2003

Related U.S. Application Data

(63) Continuation-in-part of application No. 10/290,803, filed on Nov. 8, 2002, now Pat. No. 6,630,016.
(60) Provisional application No. 60/354,062, filed on Jan. 31, 2002.

(51) Int. Cl.[7] ............................. C02F 1/50; B01D 46/00
(52) U.S. Cl. ........................... 96/226; 55/524; 210/501; 210/502.1; 210/508
(58) Field of Search ..................... 96/223, 226; 55/524; 210/501, 502.1, 504, 506, 508; 95/273, 274, 285

(56) References Cited

U.S. PATENT DOCUMENTS

| | | | | |
|---|---|---|---|---|
| 2,261,002 A | * | 10/1941 | Moore | 528/397 |
| 2,271,378 A | * | 1/1942 | Edward | 424/78.08 |
| 2,388,614 A | * | 11/1945 | Emory et al. | 514/556 |
| 2,454,547 A | * | 11/1948 | Houk et al. | 564/292 |
| 4,682,992 A | * | 7/1987 | Fuchs | 96/226 |
| 4,828,698 A | * | 5/1989 | Jewell et al. | 210/266 |
| 4,981,591 A | * | 1/1991 | Ostreicher | 210/502.1 |
| 5,006,267 A | * | 4/1991 | Vaughn et al. | 210/755 |
| 5,019,311 A | * | 5/1991 | Koslow | 264/122 |
| 5,618,622 A | * | 4/1997 | Gillberg-Laforce et al. | 428/357 |
| 5,792,513 A | * | 8/1998 | Koslow et al. | 427/195 |
| 5,876,489 A | * | 3/1999 | Kunisaki et al. | 96/226 |
| 6,190,437 B1 | * | 2/2001 | Forsyth | 95/90 |
| 6,471,876 B1 | * | 10/2002 | Hansen et al. | 210/764 |
| 6,565,749 B1 | * | 5/2003 | Hou et al. | 210/500.38 |
| 2003/0168401 A1 | * | 9/2003 | Koslow | 210/500.25 |

FOREIGN PATENT DOCUMENTS

| | | | |
|---|---|---|---|
| JP | 08193004 A | * | 7/1996 |
| WO | WO 97/23594 | * | 7/1997 |
| WO | WO 01/07090 | * | 2/2003 |

OTHER PUBLICATIONS

Koslow, E.E., "Microbiological Interception Using Modified Carbon Blocks", Sep. 26, 2002, International Activated Carbon Conference.*

Kowslow, E.E., "The Quest for the Holy Grail, Microbiological Carbon Block Filters", Water Conditioning & Purification, Aug. 2002.*

* cited by examiner

Primary Examiner—Frank M. Lawrence
(74) Attorney, Agent, or Firm—Shelly S. Ma; Kelly M. Reynolds

(57) ABSTRACT

The present invention is directed to a microporous filter medium treated with a microbiological interception enhancing agent comprising a cationic chemical having a medium to high charge density and a molecular weight greater than about 5000 Daltons, adsorbed on at least a portion of the microporous structure, and a biologically active metal in direct proximity to the cationic chemical and also on at least a portion of the microporous structure, wherein the flow of fluid through the filter medium decreases in response to an amount of polyanionic acids present in an influent. Robust microbiological interception is still maintained due to the extended empty bed contact time as a result of the diminished flow rate.

22 Claims, 4 Drawing Sheets

MICROPOROUS FILTER MEDIA WITH INTRINSIC SAFETY FEATURE

This application is a continuation-in-part of U.S. application Ser. No. 10/290,803 filed on Nov. 8, 2002, now U.S. Pat. No. 6,630,016, which claims priority from U.S. Provisional Application No. 60/354,062 filed on Jan. 31, 2002.

This invention is directed to filtration systems having an intrinsic safety feature that includes a filter medium that provides a self seal in the presence of excess natural organic matter such as polyanionic acids found in non-potable water sources.

SUMMARY OF THE INVENTION

In a first aspect, the present invention is directed to a filter medium having an intrinsic safety feature comprising: a microporous structure having a mean flow pore size of less than about 2 microns; and a microbiological interception enhancing agent comprising a cationic chemical having a medium to high charge density and a molecular weight greater than about 5000 Daltons, adsorbed on at least a portion of the microporous structure, wherein the cationic chemical forms a by-product in the presence of excess polyanionic acids in an influent thereby reducing flow through the filter medium to prevent passage of microbiological contaminants.

In another aspect, the present invention is directed to a filter medium having an intrinsic safety feature comprising: a microporous structure having a mean flow pore size of less than about 2 microns; and a microbiological interception enhancing agent comprising a cationic chemical having a medium to high charge density and a molecular weight greater than about 5000 Daltons, adsorbed on at least a portion of the microporous structure, and a biologically active metal in direct proximity to the cationic chemical wherein the biologically active metal is caused to precipitate with at least a portion of a counter ion associated with the cationic chemical, and wherein the cationic chemical forms a by-product in the presence of excess polyanionic acids in an influent thereby reducing flow through the filter medium to prevent passage of microbiological contaminants.

In yet another aspect, the present invention is directed to a method of filtering a fluid containing microbiological contaminants and polyanionic acids, comprising the steps of: providing a filter medium having an intrinsic safety feature comprising a microporous structure having a mean flow pore size of less than about 2 microns, wherein the microporous structure is treated with a microbiological interception enhancing agent comprising a cationic chemical having a medium to high charge density and a molecular weight greater than about 5000 Daltons, adsorbed on at least a portion of the microporous structure, and a biologically active metal in direct proximity to the cationic chemical also on at least a portion of the microporous structure; passing the fluid containing microbiological contaminants and polyanionic acids through the filter medium; and obtaining greater than about 4 log reduction of microbiological contaminants in an effluent, wherein a flow of fluid through the filter medium is reduced as a result of the polyanionic acids reacting with the cationic chemical, thereby preventing passage of the microbiological contaminants while retaining enhanced interception of the microbiological contaminants.

In still yet another aspect, the present invention is directed to a gravity-flow filtration system for treating, storing, and dispensing fluids comprising: a first reservoir for holding a fluid to be filtered; a filter medium in fluid communication with the first reservoir, the filter medium comprising a microporous structure with a mean flow pore size of less than about 1 micron, the filter medium treated to provide at least about 4 log reduction of microbiological contaminants smaller than the mean flow pore size of the filter medium, wherein the flow of fluid through the filter medium decreases in response to an amount of polyanionic acids present in the fluid; and a second reservoir in fluid communication with the filter medium for collecting a filtered fluid.

In still yet another aspect, the present invention is directed to a pressurized filtration system for treating, and dispensing fluids comprising: a reservoir for collecting a filtered fluid; and a filter medium in fluid communication with the reservoir, the filter medium comprising a microporous structure with a mean flow pore size of less than about 2 microns, the filter medium treated to provide at least about 4 log reduction of microbiological contaminants smaller than the mean flow pore size of the filter medium, wherein the flow of fluid through the filter medium decreases in response to an amount of polyanionic acids present in the fluid.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the description of the preferred embodiment(s) which follows taken in conjunction with the accompanying drawings in which:

DETAILED DESCRIPTION OF THE PREFERRED EMBODIMENT(S)

Figure 1:
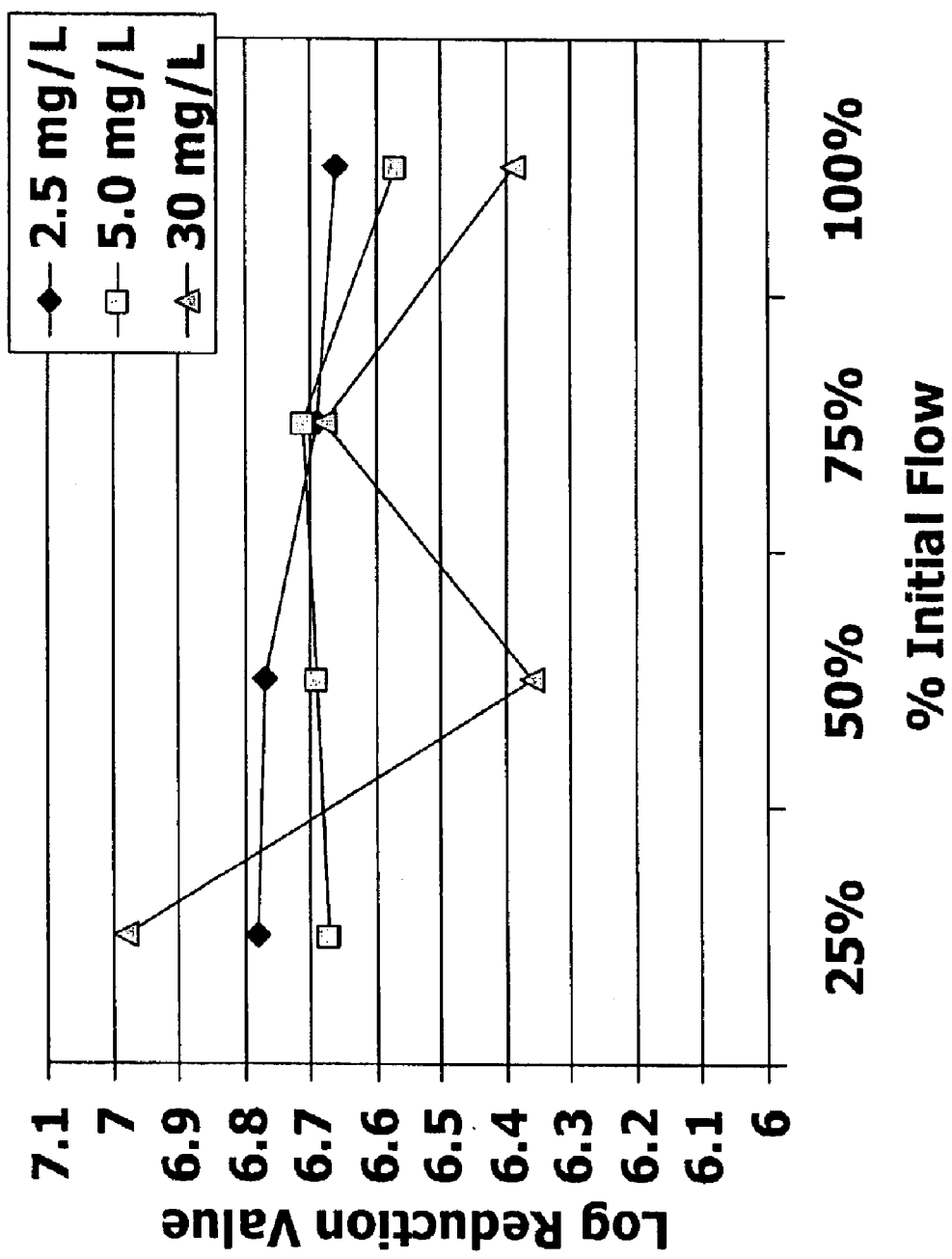
FIG. 1 is a graph plotting log reduction values of MS2 coliphage versus percentages of the initial flow rate through a filter system of the present invention.

In describing the preferred embodiment of the present invention, reference will be made herein to FIGS. 1 to 4 of the drawings.

Definitions

As used herein, "absorbent" shall mean any material that is capable of drawing a substance into its inner structure.

As used herein, "adsorbent" shall mean any material that is capable of drawing a substance to its surface by physical means and without any covalent bonding.

As used herein, "binder" shall mean a material used principally to hold other materials together.

As used herein, "contaminant reduction" shall mean attenuation of an impurity in a fluid that is intercepted, removed, and/or rendered inactive, chemically, mechanically or biologically, in order to render the fluid safer as, for example, for human use, or more useful as in industrial applications.

As used herein, "empty bed contact time" or "EBCT" shall mean a measure of how much contact occurs between particles, such as, for example, activated carbon, and a fluid as the fluid flows through the bed of particles.

As used herein, "fiber" shall mean a solid that is characterized by a high aspect ratio of length to diameter of, for example, several hundred to one. Any discussion of fibers shall also be deemed to include whiskers.

As used herein, "filter medium" shall mean a material that performs fluid filtration.

As used herein, "fluid" shall mean a liquid, gas, or combination thereof.

As used herein, "intercept" or "interception" are taken to mean interfering with, or stopping the passage of, so as to affect, remove, inactivate or influence.

As used herein, "log reduction value" or "LRV" shall mean the $\log_{10}$ of the number of organisms in the influent divided by the number of organisms in the effluent after passing through a filter.

As used herein, "mean flow pore size" shall mean the pore size of a dry filter medium wherein half of the flow through the filter medium is through pores that are larger than the mean flow pore size and half of the flow is through pores that are smaller than the mean flow pore size at a given pressure when determined using an Automated Capillary Flow Porometer available from Porous Materials, Inc., Ithaca, N.Y.

As used herein, "metal" shall mean to include the salts, colloids, precipitates, base metal, and all other forms of a given metallic element.

As used herein, "microbiological interception enhanced filter medium" shall mean a filter medium having a microporous structure where at least a portion of the microporous structure is treated with a microbiological interception enhancing agent.

As used herein, "microbiological interception enhancing agent" shall mean a cationic chemical having a counter ion associated therewith in combination with a biologically active metal.

As used herein, "microorganism" shall mean any living organism that can be suspended in a fluid, including but not limited to, bacteria, viruses, fungi, protozoa, and reproductive forms thereof including cysts and spores.

As used herein, "microporous structure" shall mean a structure that has a mean flow pore size less than about 2.0 microns, and often less than about 1.0 micron.

As used herein, "natural organic matter" or "NOM" shall mean organic matter often found in potable or non-potable water, a portion of which reduces or inhibits the streaming, or zeta, potential of a positively charged filter medium. Exemplary of NOM are polyanionic acids such as, but not limited to, humic acid and fulvic acid.

As used herein, "nonwoven" means a web or fabric or other medium having a structure of individual fibers that are interlaid, but not in a highly organized manner as in a knitted or woven fabric. Nonwoven webs generally can be prepared by methods that are well known in the art. Examples of such processes include, but are not limited to, and by way of illustration only, meltblowing, spunbonding, carding, and air laying.

As used herein, "particle" shall mean a solid having a size range from colloidal to macroscopic, and with no specific limitation on shape, but generally of a limited length to width ratio.

As used herein, "prefilter" shall mean a filter medium generally located upstream from other filtration layers, structures or devices and capable of reducing particulate contaminants prior to the influent contacting subsequent filtration layers, structures or devices.

As used herein, "whisker" shall mean a filament having a limited aspect ratio and intermediate between the aspect ratio of a particle and a fiber. Any discussion of fibers shall also be deemed to include whiskers.

The Microbiological Interception Enhanced Filter Medium

A filter medium of the present invention has an intrinsic safety feature wherein the flow of fluid through the filter medium is progressively reduced in the presence of excessive amounts of polyanionic acids that reduce the effectiveness of the filter medium in intercepting microbiological contaminants. The filter medium has a microporous structure that provides microbiological interception capability using a combination of an appropriate pore structure and a chemical treatment. The microporous structure comprises an array of active particles that have a specific pore structure, as well as adsorbent and/or absorbent properties. The array can be a solid composite block, a monolith, a ceramic candle, a flat-sheet composite of bonded or immobilized particles formed into a coherent medium using a binder or supporting fibers, and the like. These particle arrays can be made through processes known in the art such as, for example, extrusion, molding, or slip casting. The microporous structure can also comprise a plurality of nanofibers formed into a nonwoven or paper-like structure, but may include whiskers, or be a membrane. Such a microporous structure is disclosed in co-pending U.S. patent application Ser. No. 10/286,695 filed on Nov. 1, 2002, which is hereby incorporated by reference as needed.

The chemical treatment process used to treat the surface of the microporous structure utilizes a synergistic interaction between a cationic chemical and a biologically active metal, that when combined, provide broad-spectrum reduction of microbiological contaminants on contact. The charge provided by the cationic chemical to the filter medium aids in electro-kinetic interception of microbiological contaminants, while the tight pore structure provides a short diffusion path and, therefore, rapid diffusion kinetics of microbiological contaminants in a flowing fluid to a surface of the microporous structure. The microporous structure also provides supplemental direct mechanical interception of microbiological contaminants. Due to the dominant role of diffusion for the interception of extremely small particles, there is a direct correlation between the log reduction value of viral particles and the contact time of the influent within the filter medium, rather than a dependence upon the thickness of the filter medium.

Characteristics of the Microbiological Interception Enhanced Filter Medium

In order to provide full microbiological interception capability, the microbiological interception enhanced filter medium of the present invention has a mean flow pore size of less than about 2 microns, and more preferably less than or equal to about 1 micron. If the mean flow pore size is greater than about 2 microns, then the diffusion efficiency of viral particles rapidly declines and efficient biological interception fails. The volume of the microbiological interception enhanced filter medium of the present invention compared to the flow rate of fluid through the filter medium must be sufficient to provide a contact time adequate for the contaminants to diffuse to a surface of the filter medium. To provide enhanced electro-kinetic interception of microorganisms, of which the majority are negatively charged, at least a portion of the microporous structure is coated with a cationic chemical to produce a positive charge on at least a portion of such microporous structure. The cationic chemical is of sufficient molecular size to prevent fouling of the micro-pores and mezo-pores of the active particles.

Natural organic matter (NOM), such as polyanionic acids, i.e., humic acid or fulvic acid, that can reduce or remove the charge on the microbiological interception enhanced filter medium, is preferably prevented from contacting the charged microporous structure through the use of an adsorbent prefilter that substantially removes the NOM. It is possible to incorporate the NOM removing material directly into the microbiological interception enhanced filter medium, thereby eliminating the need for a separate adsorbent prefilter. Also, depending on the type of active particles used, the upstream portion of the microbiological interception enhanced filter medium itself can naturally reduce or remove NOM as well and prevent a loss of performance of the downstream portions of the microbiological interception enhanced filter medium.

In situations where excessive amounts of polyanionic acids are present, the cationic material reacts with the polyanionic acids to form a by-product that effectively reduces or curtails flow through the microbiological interception enhanced filter medium thereby preventing passage of any microbiological contaminants. Although the NOM can reduce the effectiveness of the microbiological interception enhanced filter medium, passage of microbiological contaminants is prevented as the intrinsic safety feature of the filter medium of the present invention reduces the flow rate of the influent passing through the filter medium. As the flow rate is reduced, the empty bed contact time (EBCT) of fluid flowing through the filter medium increases. Although the charge on the filter medium may be reduced, the prolonged EBCT allows enhanced microbiological interception to take place. As the by-product builds up in the filter medium due to the increasing total load of polyanionic acids in the filter medium, the flow of fluid through the filter medium drops to an unacceptable rate in response to the amount of polyanionic acids present in the fluid, and eventually shuts down the filter medium, thereby indicating to a user that the filter medium needs replacement.

When used in the context of a gravity-flow water filtration system, it is preferable that the microbiological interception enhanced filter medium be made with hydrophilic materials or treated with a wetting agent to provide good, spontaneous wettability. Alternatively, in other applications, the microbiological interception enhanced filter medium can be treated to provide either a hydrophilic or hydrophobic characteristic as needed. It is possible that the microbiological interception enhanced filter medium can have both positively and negatively charged and uncharged regions, and/or hydrophilic and hydrophobic regions. For example, the negatively charged regions can be used to enhance the interception of less common positively charged contaminants and uncharged hydrophobic regions can be used to provide enhanced interception of contaminants that are attracted to hydrophobic surfaces.

The Active Particles

The microbiological interception enhanced filter medium having enhanced microbiological interception capabilities of the present invention comprises an array of adsorbent and/or absorbent active particles having a particle size distribution of 80×325 mesh with about 20% to about 24% pan (particles smaller than −325 mesh). The active particles can include, but are not limited to, activated carbon, activated alumina, zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, super absorbent polymers (SAPs), and combinations thereof. A microbiological interception enhanced filter medium having requisite properties can be obtained by combining one or more of these active particles.

One preferred microporous structure comprises active particles of activated carbon that naturally resist fouling by NOM and is efficient at adsorbing the potentially interfering NOM in peripheral regions of the microporous structure while protecting inner regions. Preferably, the activated carbon is acid washed bituminous coal-based activated carbon. Commercially available activated carbon suitable for use in the present invention can be obtained from Calgon Carbon Corporation of Pittsburgh, Pa., under the trade designation TOG-NDS or from California Carbon Company of Wilmington, Calif., under the trade designation 1240ALC. Most preferably, the active particles are comprised of acid washed bituminous coal-based activated carbon from Calgon Carbon Corporation, having a particle size distribution as follows: about 3% to about 7%, preferably about 5%, 80 mesh size particles; about 12% to about 18%, preferably about 15% 100 mesh; about 44% to about 50%, preferably 47% 200 mesh; about 8% to about 14%, preferably about 11% 325 mesh; and about 20% to about 24% pan, preferably about 22% pan.

The Microbiological Interception Enhancing Agent

The active particles of the microporous structure are chemically treated with a microbiological interception enhancing agent capable of creating a positive charge on the surface of the active particles. The chemical treatment produces a strong positive charge upon the treated surfaces as measured using streaming potential analysis and this positive charge is retained at pH values below 10. A cationic metal complex is formed on at least a portion of the surface of the active particles by treating the active particles with a cationic chemical. The cationic chemical may be a small charged molecule or a linear or branched polymer having positively charged atoms along the length of the polymer chain.

If the cationic chemical is a polymer, the charge density is preferably greater than about 1 charged atom per about every 20 Angstroms, preferably greater than about 1 charged atom per about every 10 Angstroms, and more preferably greater than about 1 charged atom per about every 5 Angstroms of molecular length. The higher the charge density on the cationic chemical, the higher the concentration of the counter ion associated therewith. A high concentration of an appropriate counter ion can be used to drive the precipitation of a metal complex. The high charge density of the cationic polymer provides the ability to adsorb and significantly reverse the normal negative charge of active particles such as carbon. The cationic chemical should consistently provide a highly positively charged surface to the microporous structure as determined by a streaming or zeta potential analyzer, whether in a high or low pH environment.

The use of a polymer of sufficiently high molecular weight allows treatment of the surfaces of the active particles without serious attendant impact upon the adsorptive capabilities of the mezo-pores and micro-pores of the active particles. The cationic chemical can have a molecular weight greater than or equal to about 5000 Daltons, preferably greater than or equal to 100,000 Dalton, more preferably greater than or equal to about 400,000 Daltons, and can be greater than or equal to about 5,000,000 Daltons.

The cationic chemical includes, but is not limited to, quaternized amines, quaternized amides, quaternary ammonium salts, quaternized imides, benzalkonium compounds, biguanides, cationic aminosilicon compounds, cationic cellulose derivatives, cationic starches, quaternized polyglycol amine condensates, quaternized collagen polypeptides, cationic chitin derivatives, cationic guar gum, colloids such as cationic melamine-formaldehyde acid colloids, inorganic treated silica colloids, polyamide-epichlorohydrin resin, cationic acrylamides, polymers and copolymers thereof, combinations thereof, and the like. Charged molecules useful for this application can be small molecules with a single charged unit and capable of being attached to at least a portion of the microporous structure. The cationic chemical preferably has one or more counter ions associated therewith which, when exposed to a biologically active metal salt solution, cause preferential precipitation of the metal in proximity to the cationic surface to form a cationic metal precipitate complex.

Exemplary of amines may be pyrroles, epichlorohydrin derived amines, polymers thereof, and the like. Exemplary of amides may be those polyamides disclosed in International Patent Application No. WO 01/07090, and the like. Exemplary of quaternary ammonium salts may be homopolymers of diallyl dimethyl ammonium halide, epichlorohydrin derived polyquaternary amine polymers, quaternary ammonium salts derived from diamines and dihalides such as those disclosed in U.S. Pat. Nos. 2,261,002, 2,271,378, 2,388,614, 2,454,547, all of which are incorporated by reference, and in International Patent Application No. WO 97/23594, polyhexamethyldimethlyammonium bromide, and the like. The cationic chemical may be chemically bonded, adsorbed, or crosslinked to itself and/or to the active particles.

Furthermore, other materials suitable for use as the cationic chemical include BIOSHIELD® available from BioShield Technologies, Inc., Norcross, Ga. BIOSHIELD® is an organosilane product including approximately 5% by weight octadecylaminodimethyltrimethoxysilylpropyl ammonium chloride and less than 3% chloropropyltrimethoxysilane. Another material that may be used is SURFACINE®, available from Surfacine Development Company LLC, Tyngsboro, Mass. SURFACINE® comprises a three-dimensional polymeric network obtained by reacting poly(hexamethylenebiguanide) (PHMB) with 4,4'-methlyene-bis-N,N-dilycidylaniline (MBGDA), a crosslinking agent, to covalently bond the PHMB to a polymeric surface. Silver, in the form of silver iodide, is introduced into the network, and is trapped as submicron-sized particles. The combination is an effective biocide, which may be used in the present invention. Depending upon the active particles, the MBGDA may or may not crosslink the PHMB to the microporous structure.

The cationic chemical is exposed to a metal salt solution such that the metal is in direct proximity to the cationic chemical wherein the metal is caused to precipitate with at least a portion of a counter ion associated with the cationic chemical onto at least a portion of the surface of at least some of the microporous structure. For this purpose, the metals that are biologically active are preferred. Such biologically active metals include, but are not limited to, silver, copper, zinc, cadmium, mercury, antimony, gold, aluminum, platinum, palladium, and combinations thereof. The most preferred biologically active metals are silver and copper. The biologically active metal salt solution is preferably selected such that the metal and the counter ion of the cationic chemical are substantially insoluble in an aqueous environment to drive precipitation of the metal precipitate. Preferably, the metal is present in an amount of about 0.01% to about 2.0% by weight of the total composition.

A particularly useful microbiological interception enhancing agent is a silver-amine-halide complex. The cationic amine is preferably a homopolymer of diallyl dimethyl ammonium halide having a molecular weight of about 400,000 Daltons or other quaternary ammonium salts having a similar charge density and molecular weight. A homopolymer of diallyl dimethyl ammonium chloride useful in the present invention is commercially available from Nalco Chemical Company of Naperville, Ill., under the tradename MERQUAT® 100. The chloride counter ion may be replaced with a bromide or iodide counter ion. When contacted with a silver nitrate solution, the silver-amine-halide complex precipitates on at least a portion of the active particles of the microporous structure of the microbiological interception enhanced filter medium.

Where the active particles comprise activated carbon, the cationic chemical preferably has a high charge density and a sufficiently high molecular weight to create a strong attraction and high coordination energy with the negatively charged surface groups of activated carbon. Also, the enhanced interception using the charged surface of the activated carbon, in the presence of a colloid of a biologically active metal, is supplemented by the hydrophobic adsorption mechanism of the activated carbon. This hydrophobic mechanism is generally resistant to the impact of fouling by NOM, and is actually more effective under conditions of high ionic strength. Untreated portions of the carbon surface, with their oxygen-rich chemistry, tend to have a negative charge that can continue to adsorb positively charged particles. The combination of positive, negative, and hydrophobic surfaces presents a nearly insurmountable barrier for small particles to navigate. After treating the carbon with the microbiological interception enhancing agent, the presence of the biologically active metal and its associated counter ion on the active particles can be detected using X-ray fluorescence.

Method Of Making The Microbiological Interception Enhanced Filter Medium

The microbiological interception enhanced filter medium of the present invention can be made in accordance with processes known to one of skill in the art. Such processes include extrusion, molding, slip casting, immobilizing the active particles on a substrate, and the like. Exemplary processes are disclosed in U.S. Pat. Nos. 5,019,311, and 5,792,513.

The active particles are treated with the cationic chemical using means known to one of skill in the art such as, for example, spray coating. Preferably, the active particles are coated with about 0.5% to about 3% by weight, and more preferably about 1% by weight of the total weight of the microbiological interception enhanced filter medium. Once the cationic chemical is coated onto at least a portion of the active particles, the particles are exposed to the biologically active metal salt. A solution of the metal salt is infiltrated into the particles to cause precipitation of the biologically active metal on at least a portion of the surface of the active particles. The precipitation process accurately deposits the majority of the metal colloid directly adjacent to the cationic coating because the counter-ion associated with this coating reacts with the applied metal salt to form the colloidal particles. The metal salt can be sprayed onto the treated particles or otherwise applied using methods known to one of skill in the art. Solutions of the cationic chemical and the metal salt are preferably made with nearly ion-free water so that the counter-ions associated with the cationic chemical are drawn tightly against the cationic surface of the treated active particles and to eliminate unwanted ions that may cause uncontrolled precipitation of the biologically active metal into sites remote from the cationic surface.

Excess moisture is then removed from the particles, generally with heating or under vacuum, to a desired moisture content. Preferably, the moisture content should be less than about 10%, and more preferably less than about 5%, if the particles are to be subsequently extruded or molded using a thermoplastic binder.

Once the microbiological interception enhancing agent is coated on to at least a portion of the active particles, the active particles are ground to the desired size and potentially mixed with the binder material to form a homogenous mixture prior to immobilizing the active particles into a desired final form having the required microporous structure. The binder is chosen such that the melting point of the binder material is sufficiently lower than the melting point of the active particles so that the microbiological interception enhanced filter medium can be heated to activate the binder material, while the microporous structure does not melt and thereby lose porosity. The binder particles are preferably sufficiently evenly distributed throughout the active particles such that later, upon conversion to the microporous structure, the binder particles will entrap or bond to substantially all the active particles.

Binder materials useful in the present invention in coalescing the active particles into the microporous structure can potentially include any thermoplastic or thermoset material known in the art in either fiber, powder or particulate form. Useful binder materials can include materials such as, but not limited polyolefins, polyvinyl halides, polyvinyl esters, polyvinyl ethers, polyvinyl sulfates, polyvinyl phosphates, polyvinyl amines, polyamides, polyimides, polyoxidiazoles, polytriazols, polycarbodiimides, polysulfones, polycarbonates, polyethers, polyarylene oxides, polyesters, polyarylates, phenol-formaldehyde resins, melamine-formaldehyde resins, formaldehyde-ureas, ethyl-vinyl acetate copolymers, co-polymers and block interpolymers thereof, and combinations thereof. Variations of the above materials and other useful polymers include the substitution of groups such as hydroxyl, halogen, lower alkyl groups, lower alkoxy groups, monocyclic aryl groups, and the like.

A more detailed list of binders which can be useful in the present invention include end-capped polyacetals, such as poly(oxymethylene) or polyformaldehyde, poly(trichloroacetaldehyde), poly(n-valeraldehyde), poly(acetaldehyde), and poly(propionaldehyde); acrylic polymers, such as polyacrylamide, poly(acrylic acid), poly(methacrylic acid), poly(ethyl acrylate), and poly(methyl methacrylate); fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), and poly(vinyl fluoride); polyamides, such as poly(6-aminocaproic acid) or poly(e-caprolactam), poly(hexamethylene adipamide), poly(hexamethylene sebacamide), and poly(11-aminoundecanoic acid); polyaramides, such as poly(imino-1,3-phenyleneiminoisophthaloyl) or poly(m-phenylene isophthalamide); parylenes, such as poly-2-xylylene, and poly(chloro-1-xylylene); polyaryl ethers, such as poly(oxy-2,6-dimethyl-1,4-phenylene) or poly(p-phenylene oxide); polyaryl sulfones, such as poly(oxy-1,4-phenylenesulfonyl-1,4-phenyleneoxy-1,4-phenyl-eneisopropylide ne-1,4-phenylene), and poly(sulfonyl-1,4-phenylene-oxy-1,4-phenylenesulfonyl4,4'-biphenylene); polycarbonates, such as poly-(bisphenol A) or poly(carbonyldioxy-1,4-phenyleneisopropylidene-1,4-phenylene); polyesters, such as poly(ethylene terephthalate), poly(tetramethylene terephthalate), and poly(cyclohexyl-ene-1,4-dimethylene terephthalate) or poly(oxymethylene-1,4-cyclohexylenemethyleneoxyterephthaloyl); polyaryl sulfides, such as poly(p-phenylene sulfide) or poly(thio-1,4-phenylene); polyimides, such as poly(pyromellitimido-1,4-phenylene); polyolefins, such as polyethylene, polypropylene, poly(1-butene), poly(2-butene), poly(1-pentene), poly(2-pentene), poly(3-methyl-1-pentene), and poly(4-methyl-1-pentene); vinyl polymers, such as poly(vinyl acetate), poly(vinylidene chloride), and poly(vinyl chloride); diene polymers, such as 1,2-poly-1,3-butadiene, 1,4-poly-1,3-butadiene, polyisoprene, and polychloroprene; polystyrenes; and copolymers of the foregoing, such as acrylonitrilebutadiene-styrene (ABS) copolymers. Polyolefins that can be useful include polyethylene, linear low density polyethylene, polypropylene, poly(1-butene), poly(2-butene), poly(1-pentene), poly(2-pentene), poly(3-methyl-1-pentene), poly(4-methyl-1-pentene), and the like.

Other potentially applicable materials include polymers such as polystyrenes and acrylonitrile-styrene copolymers, styrene-butadiene copolymers, and other non-crystalline or amorphous polymers and structures.

Preferred binder materials include polyethylene, poly(ethylene vinyl acetate), and nylons. Especially preferred as a binder is grade FN 510 microfine polyethylene commercially available from Equistar Chemicals, L.P., Tuscola, Ill., under the trade designation MICROTHENE® F.

The binder can have an average particle size of about 0.1 micron to about 250 microns, preferably about 1 micron to about 100 microns, and more preferably about 5 microns to about 20 microns. It is preferable that the binder material have a softening point that is significantly lower than a softening point of the active particles so that the microbiological interception enhanced filter medium can be heated to activate the binder material, while the microporous structure does not melt and thereby lose porosity.

The amount of binder material used is dependent upon how the microporous structure is formed whether by extrusion, molding, or other processes. For example, when the active particles are extruded or molded into a solid composite block, the binder material is preferably present in an amount of about 15% to about 22% by weight, and more preferably about 17% to about 19% by weight of the microbiological interception enhanced filter medium. When the active particles are immobilized on a substrate such as, for example, a nonwoven material, the binder material is preferably present in an amount of about 5% to about 20%, and preferably about 9% to about 15% by weight of the total composition.

One or more additives either in a particulate, fiber, whisker, or powder form may also be mixed with the active particles to aid in adsorption or absorption of other contaminants or participate in the formation of the microporous structure and interception of microbiological contaminants. Useful additives may include, but are not limited to, metallic particles, activated alumina, activated carbon, silica, polymeric powders and fibers, glass beads or fibers, cellulose fibers, ion-exchange resins, engineered resins, ceramics, zeolites, diatomaceous earth, activated bauxite, fuller's earth, calcium sulfate, other adsorbent or absorbent materials, or combinations thereof. The additives can also be chemically treated to impart microbiological interception capabilities depending upon the particular application. Such additives are preferably present in a sufficient amount such that the fluid flow in the resultant microbiological interception enhanced filter medium is not substantially impeded when used in filtration applications. The amount of additives is dependent upon the particular use of the filtration system.

The final microporous structure can also be formed by slip casting or wet-forming the particles or fibers or such mixtures and subsequently causing binders or particles to sinter the ingredients together. In some cases, the particles can form their own binder as in bi-component fibers or low melting point resins. In some cases, the binder can be water soluble or cross-linkable resins or salts that when allowed to dry, or heated, or allowed to react, form the required bonds. Chemical binders can also be used as well as precipitated binders such as certain phosphate salts.

Alternatively, the microporous structure can be made using nanofibers in accordance with co-pending U.S. patent application Ser. No. 10/286,695.

Filtration Systems Utilizing the Microbiological Interception Enhanced Filter Medium The microbiological interception enhanced filter medium of the present invention can be easily incorporated into prior art filtration systems that utilize particulate filtration medium immobilized as solid composite blocks, flat, spiral or pleated sheets, monoliths, or candles. Preferably, a particulate pre-filter is used in conjunction with the microbiological interception enhanced filter medium, positioned upstream from the microbiological interception enhanced filter medium, to remove as many particulate contaminants from the influent as possible prior to the influent contacting the microbiological interception enhanced filter medium.

EXAMPLES

The following examples are provided to illustrate the present invention and should not be construed as limiting the scope of the invention.

Porometry studies were performed with an Automated Capillary Flow Porometer available from Porous Materials, Inc., Ithaca, N.Y. Parameters determined, using standard procedures published by the equipment manufacturer, include mean flow pore size and gas (air) permeability. The flow of air was assayed at variable pressure on both the dry and wet microbiological interception enhanced filter medium.

Bacterial challenges of the microbiological interception enhanced filter media were performed using suspensions of *Klebsiella terrigena* ATCC No. 33527 to evaluate the response to a bacterial challenge. The response to viral challenges were evaluated using MS2 coliphage ATTC No. 15597-B1 and PRD-1 ATCC No. 19585-B1. The Standard Operating Procedures of the ATCC were used for propagation of the bacterium and bacteriophage, and standard microbiological procedures, as well known in the art, were used for preparing and quantifying the microorganisms in both the influent and effluent of filters challenged with suspensions of the microorganisms.

Individual filters were tested in duplicate with each microorganism under a modified version of the NSF International Standard 53 cyst reduction test protocol. This protocol is designed to assess the performance of filters during an accelerated exposure to fine particulates to simulate accumulation of dirt. Filters were flushed with reverse osmosis/deionized (RO/DI) water and calibrated to an initial flow rate of 0.5 to 1.0 gallon/minute (gpm). The mean flow pore size of the filter media all were about 0.9 microns to 1.1 microns.

During testing, initial samples were drawn from both the influent and effluent sampling ports during the startup system flushing period to ensure that there was no background interference from an improperly disinfected test apparatus. The filter was then challenged with suspensions of the microorganisms, with samples being taken following a minimum 2L challenge solution, ensuring passage of the challenge water through the entire test stand prior to sampling.

All influent and effluent samples were serially diluted, as required, and plated in triplicate. In certain cases, carbon blocks of a given design were tested at several flow rates to ascertain their response to changing flow rate.

Activated carbon block filters having enhanced microbiological interception capability were prepared as follows. Twenty (20) pounds of 12×40 mesh acid-washed bituminous-coal-based activated carbon, Grade TOG-NDS, obtained from Calgon Carbon Company, was gently mixed with a solution of 1% MERQUAT® 100 in de-ionized water to thoroughly coat the carbon particles and ensure that the MERQUAT® 100 had adsorbed onto at least a portion of the carbon particles. Thereafter, a solution of silver nitrate, 35 g crystalline silver nitrate in 1.0 L de-ionized water, was added to the MERQUAT® treated carbon to allow precipitation of the silver on at least a portion of the surface of the carbon particles in the form of silver chloride colloid. The silver nitrate solution provides 0.25 wt. % silver. The treated carbon particles were dried at 135° C. until there was less than 5% moisture present in the carbon particles. Drying times varied between about 3 to about 5 hours. The dried carbon was ground in a double-roll grinder to 80×325 mesh size with approximately 14 wt. % −325 mesh pan, and was mixed with approximately 17 wt. % MICROTHENE® FN510, a low density polyethylene binder material. The mixture was extruded under suitable heat, pressure and temperature conditions, as described in U.S. Pat. No. 5,019,311. Resulting carbon block filters of various sizes were used to construct water filter systems by applying suitable end caps using a hot melt resin, as is well known in the art.

The filters were assayed for microbiological interception performance after the flow was reduced by 25%, 50% and 75% in comparison to the flow rate measured on the original, clean filter.

Examples 1 to 3
The Effect of Humic Acid Loading on Initial Flow Rates

Filter systems containing extruded carbon block filter media, 2.6 in (6.6 cm) O.D.×1.25 in (3.2 cm) I.D.×9.30 in (23.6 cm) Length, made in accordance with the procedure described above, each having an initial flow rate of 0.60 gallons/minute, were challenged with different concentrations of humic acid solutions followed by microbiological challenges. The flow rate of the filter systems decreased as the total amount of humic acid increased.

Table I shows the total amount of humic acid needed to decrease the flow rate of the filter system by 75%.

TABLE I

Humic Acid Loading v. % Initial Flow Rate

| Example % Reduction in Flow | 1[a] Tot. Vol. Passed | 2[b] Tot. Vol. Passed | 3[c] Tot. Vol. Passed |
| --- | --- | --- | --- |
| 25% (0.45 gal/min) | 15.5 gal. | 4 gal. | 3 gal |
| 50% (0.30 gal/min) | 19 gal. | 8 gal. | 6 gal. |
| 75% (0.15 gal/min) | 26.5 gal. | 11 gal. | 7 gal. |
| Total Humic Acid Loading to Achieve 75% Flow Reduction | 250 mg | 208 mg | 794 mg | a = 2.5 mg/L Humic Acid Challenge;
b = 5 mg/L Humic Acid Challenge;
c = 30 mg/L Humic Acid Challenge As the filter media is exposed to an increasing amount of humic acid, the flow rates steadily decline to an unacceptable value. It is hypothesized that the high molecular weight cationic chemical reacts with the humic acid, or other polyanionic acids present, forming a by-product that reduces the flow of fluid through the filter medium, and eventually shuts down the flow.

Figure 2:
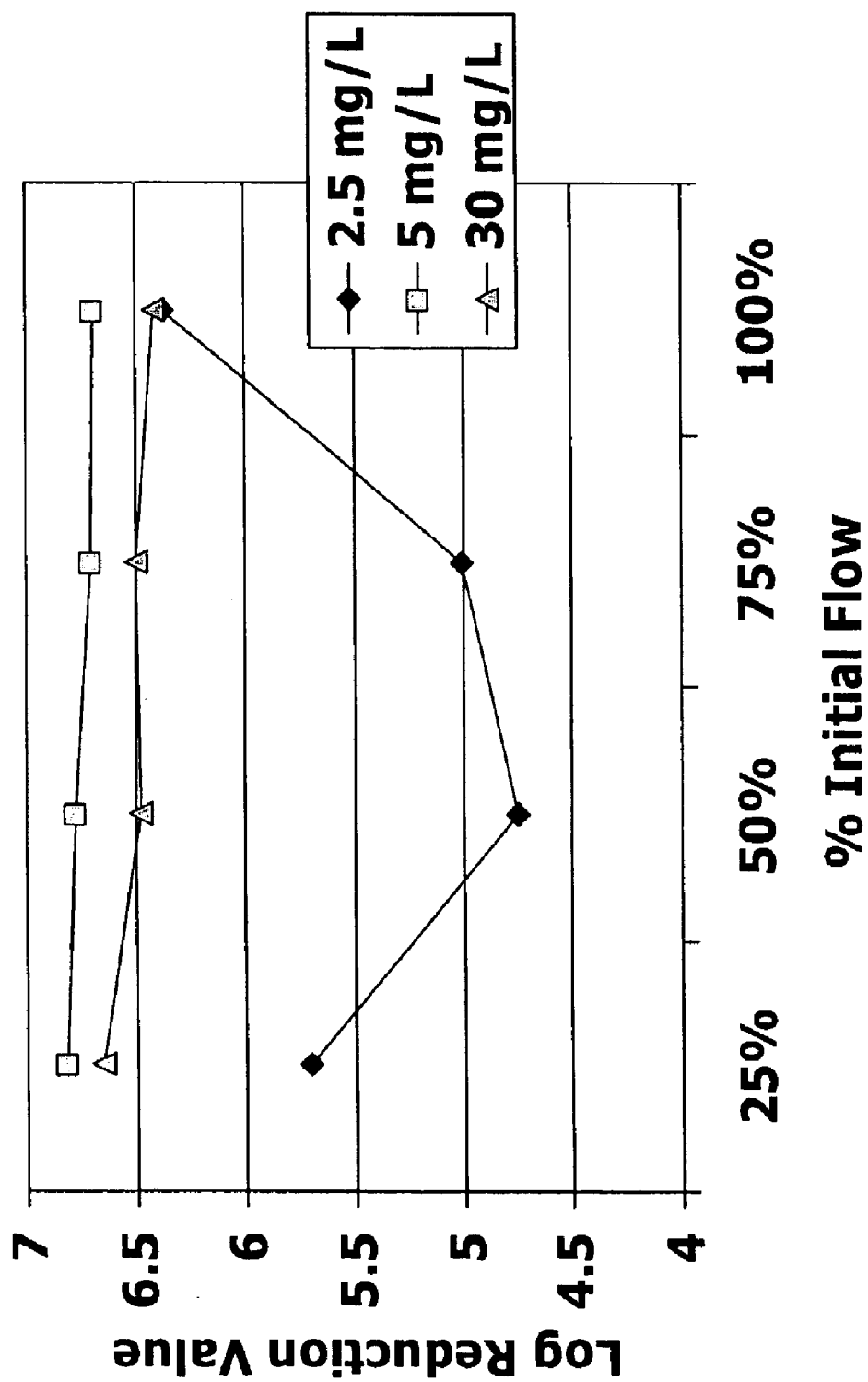
FIG. 2 is a graph plotting log reduction values of PRD-1 versus percentages of the initial flow rate through a filter system of the present invention.
Figure 3:
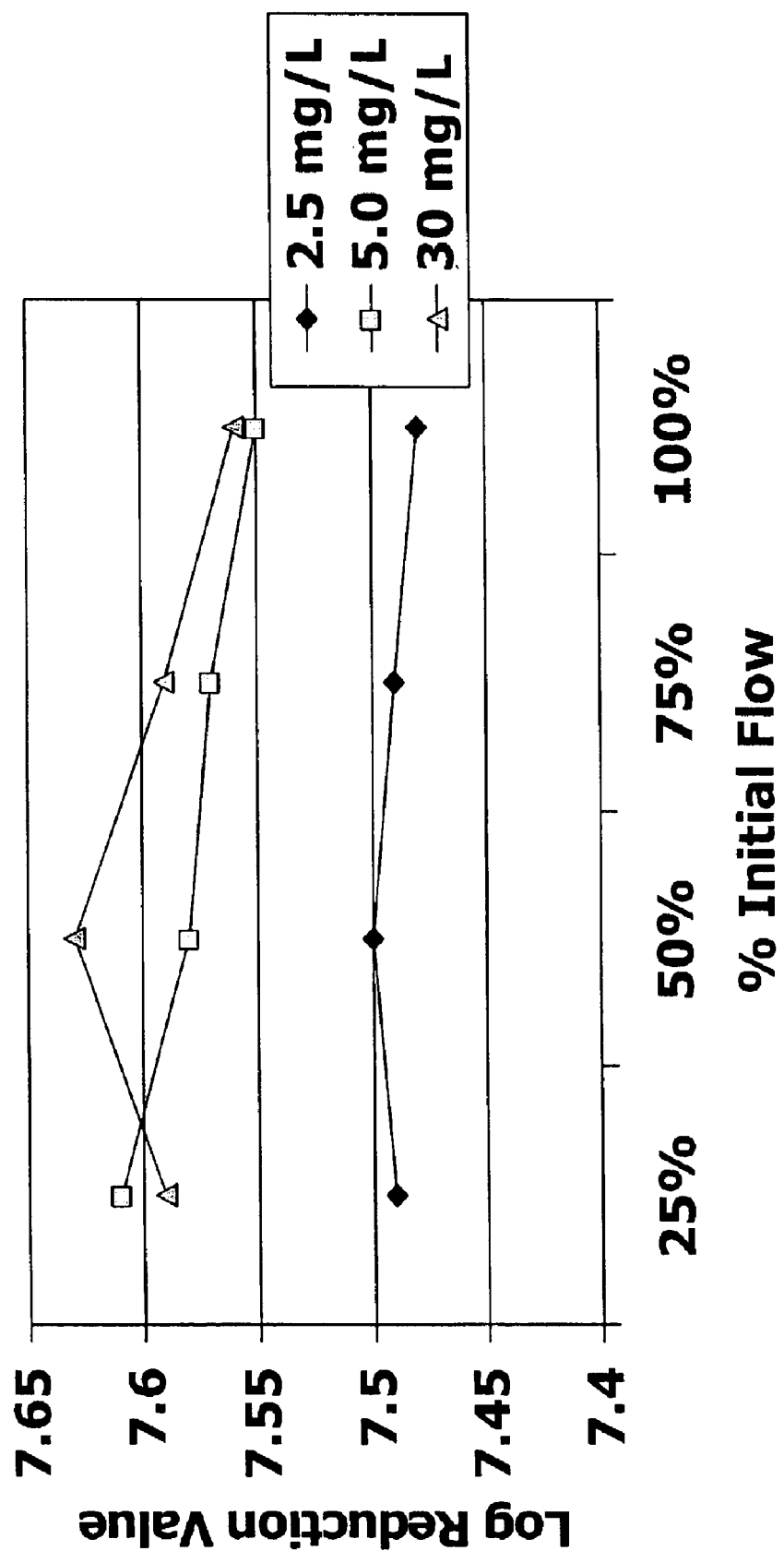
FIG. 3 is a graph plotting log reduction values of *Klebsiella terrigena* versus percentages of the initial flow rate through a filter system of the present invention.

Even in the presence of humic acid, the filter media still provided acceptable log reduction values of intermittent three organism cocktails of MS2, PRD-1, and *K. terrigena* prepared with a humic acid solution (2.5 mg/L RO/DI water). Effluents were collected in sterile 250 ml Erlenmeyer flasks, diluted and plated on petri dishes following standard procedures and left overnight. Before and after each challenge, the humic acid solutions were passed through each filter. In FIG. 1, the filter media provided log reduction values of greater than about 6.3 when challenged with MS2 at all concentrations of humic acid. In FIG. 2, the filter media provided log reduction values of greater than about 4.5 when challenged with PRD-1. In FIG. 3, the filter media provided log reduction values of greater than about 7.4 when challenged with *K. terrigena*.

Examples 4 to 10
The Linear Relationship Between Log Reduction Values of Microbiological Contaminants and Empty Bed Contact Time Filter systems containing extruded carbon block filter media were made in accordance with the procedure described above, but wherein 70 g of silver nitrate was used to treat the MERQUAT® treated carbon providing 0.5 wt. % silver. The filters were assayed for microbiological interception performance. The efficacy of the filter medium of the present invention is shown in Table II below.

TABLE II

LRVs Of Microbiological Interception Enhanced Activated Carbon Block Filter Medium

| Ex # | Filter Size O.D. × I.D. × Length (inches) | Flow Rate (gpm) | B. diminuta (LRV) | E. coli (LRV) | B. subtilis (LRV) | MS2 (LRV) |
|---|---|---|---|---|---|---|
| 4 | 1.85 × 0.375 × 2.94 | 0.50 | | | | 3.82 |
| 5 | 1.85 × 0.50 × 2.94 | 0.75 | | | | 2.15 |
| 6 | 2.25 × 1.00 × 4.00 | 0.50 | 8.49 | 8.88 | 8.97 | 8.35 |
| 7 | 2.40 × 1.19 × 9.628 | 1.0 | | | | 5.79 |
| 8 | 1.50 × 0.375 × 6.055 | 0.50 | 8.80 | | | 5.31 |
| 9 | 1.50 × 0.375 × 6.055 | 0.60 | | | | 3.51 |
| 10 | 1.50 × 0.375 × 6.055 | 0.75 | | 8.79 | | 3.16 |

Figure 4:
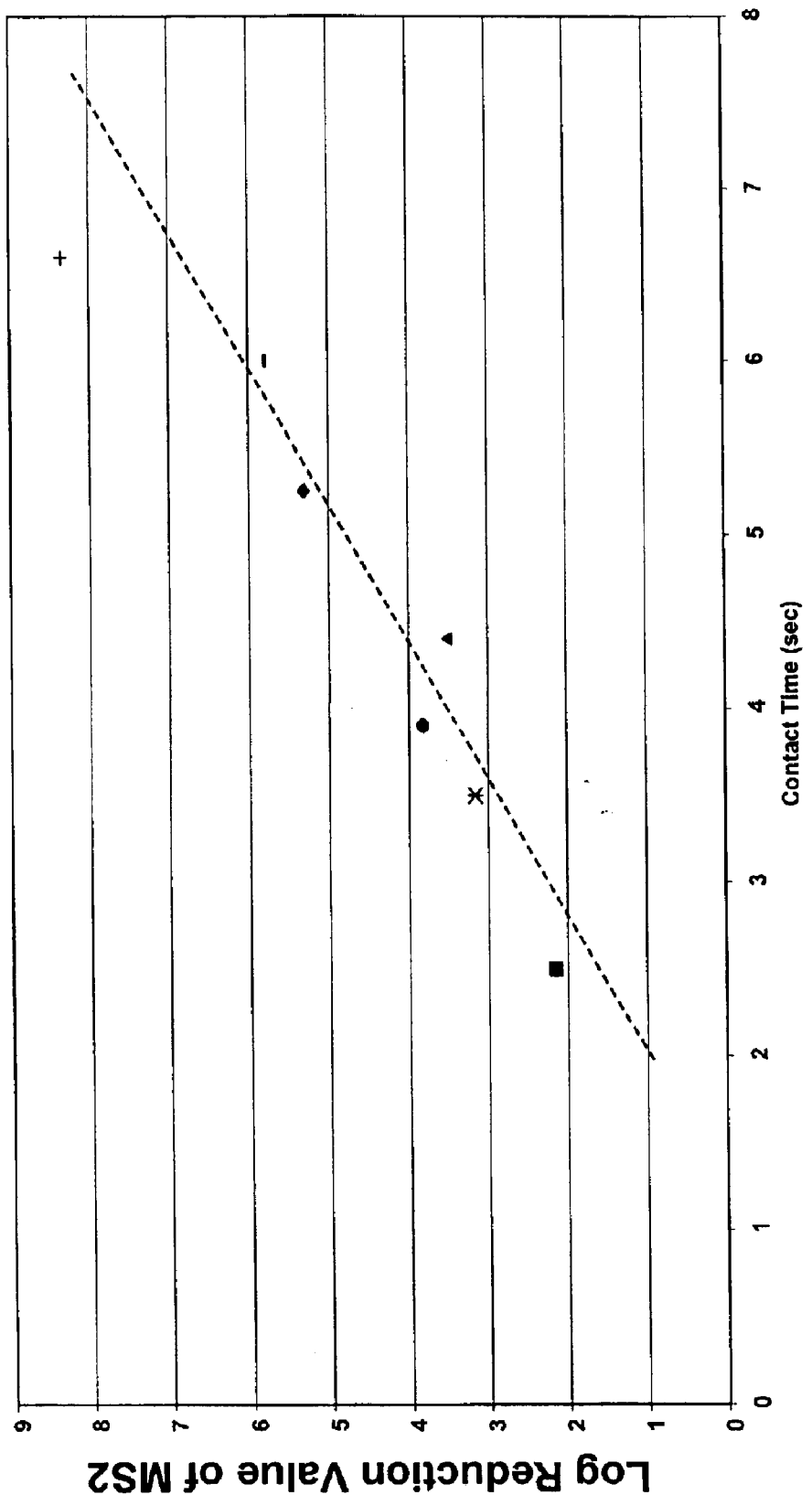
FIG. 4 is a graph plotting the empty bed contact time versus the log reduction values of MS2 bacteriophage of a filter medium of the present invention.

The activated carbon block filter medium of the present invention provides greater than 8 log reduction of larger organisms such as *B. diminuta, E. coli* and *B. subtilis*. In fact, interception of these organisms was beyond the sensitivity of the test protocol in all cases. The results for MS2 penetration show no apparent correlation between wall thickness and levels of interception. This indicates that a traditional mechanical interception mechanism is not responsible for MS2 interception, but rather a direct relationship between the log interception and the empty bed contact time (EBCT) of the filter. FIG. 4 shows a substantially linear relationship between log reduction values of MS2 and the EBCT of the filter indicating a diffusive interception mechanism with a requirement of approximately 6 seconds EBCT in order to achieve effective reduction of this bacteriophage in a microbiological interception enhanced filter medium having a mean flow pore size of about 0.9 to about 1.1 microns.

The diffusive nature of the filter media of the present invention provides a direct relationship between the log interception and the EBCT of the filter. The substantially linear relationship between log reduction values of microbiological contaminants and the EBCT suggests that as the total amount of humic acid passes through the filter system, and the flow rate diminishes, reduction of microbiological contaminants is still maintained due to the extended EBCT. Robust microbiological interception is still achieved even with prolonged exposure to humic acid or other polyanionic acids that have reduced the efficacy of the filter medium in intercepting microbiological contaminants.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A filter medium comprising:
   a microporous structure having a mean flow pore size of less than about 2 microns; and
   a microbiological interception enhancing agent comprising a cationic chemical having a medium to high charge density and a molecular weight greater than about 5000 Daltons, adsorbed on at least a portion of said microporous structure and a biologically active metal in direct proximity to the cationic chemical, wherein the cationic chemical forms a by-product in the presence of excess polyanionic acids in an influent thereby reducing flow through said filter medium to prevent passage of microbiological contaminants.

2. A filter medium of claim 1 wherein said microporous structure comprises an array of particles, and the cationic chemical comprises a high molecular weight polymer.

3. A filter medium of claim 1 wherein said microporous structure comprises a plurality of fibers having a mean flow pore size of less than or equal to about 1 micron.

4. A filter medium of claim 1 wherein said biologically active metal is caused to precipitate with at least a portion of a counter ion associated with the cationic chemical.

5. A filter medium of claim 4 wherein the biologically active metal comprises silver, copper, zinc, cadmium, mercury, antimony, gold, aluminum, platinum, palladium, or combinations thereof.

6. A filter medium of claim 1 wherein the flow of a fluid through said filter medium decreases in response to an amount of polyanionic acids present in the influent.

7. A filter medium of claim 6 wherein said filter medium retains enhanced interception of microbiological contaminants.

8. A filter medium comprising:
a microporous structure having a mean flow pore size of less than about 2 microns; and
a microbiological interception enhancing agent comprising a cationic chemical having a medium to high charge density and a molecular weight greater than about 5000 Daltons, adsorbed on at least a portion of said microporous structure, and a biologically active metal in direct proximity to the cationic chemical wherein the biologically active metal is caused to precipitate with at least a portion of a counter ion associated with the cationic chemical, and wherein the cationic chemical forms a by-product in the presence of excess polyanionic acids in an influent thereby reducing flow through said filter medium to prevent passage of microbiological contaminants.

9. A filter medium of claim 8 wherein the biologically active metal comprises silver.

10. A filter medium of claim 8 wherein the flow of a fluid through said filter medium decreases in response to an amount of polyanionic acids present in the influent.

11. A filter medium of claim 8 wherein said filter medium retains enhanced interception of microbiological contaminants.

12. A gravity-flow filtration system for treating, storing, and dispensing fluids comprising:
a first reservoir for holding a fluid to be filtered;
a filter medium in fluid communication with said first reservoir, said filter medium comprising a microporous structure with a mean flow pore size of less than about 1 micron and a microbiological interception enhancing agent comprising a cationic chemical and a biologically active metal in direct proximity to the cationic chemical, said filter medium treated to provide at least about 4 log reduction of microbiological contaminants smaller than the mean flow pore size of said filter medium, wherein the flow of fluid through said filter medium decreases in response to an amount of polyanionic acids present in the fluid; and
a second reservoir in fluid communication with said filter medium for collecting a filtered fluid.

13. A gravity-flow filtration system of claim 12 wherein said filter medium retains enhanced interception of the microbiological contaminants.

14. A pressurized filtration system for treating, and dispensing fluids comprising:
a reservoir for collecting a filtered fluid; and
a filter medium in fluid communication with said reservoir, said filter medium comprising a microporous structure with a mean flow pore size of less than about 2 microns and a microbiological interception enhancing agent comprising a cationic chemical and a biologically active metal in direct proximity to the cationic chemical, said filter medium treated to provide at least about 4 log reduction of microbiological contaminants smaller than the mean flow pore size of said filter medium, wherein the flow of fluid through said filter medium decreases in response to an amount of polyanionic acids present in the fluid.

15. A pressurized filtration system of claim 14 wherein said filter medium retains enhanced interception of the microbiological contaminants.

16. A filter medium comprising:
a microporous structure having a mean flow pore size of less than about 2 microns; and
a microbiological interception enhancing agent comprising a cationic chemical having a medium to high charge density and a molecular weight greater than about 5000 Daltons, adsorbed on at least a portion of said microporous structure, and a counter ion associated with said cationic chemical wherein at least a portion of the counter ion comprises bromide, iodide or chloride, wherein the cationic chemical forms a by-product in the presence of excess polyanionic acids in an influent thereby reducing flow through said filter medium to prevent passage of microbiological contaminants.

17. A filter medium of claim 16 wherein said microporous structure comprises an array of particles, and the cationic chemical comprises a high molecular weight polymer.

18. A filter medium of claim 16 wherein said microporous structure comprises a plurality of fibers having a mean flow pore size of less than or equal to about 1 micron.

19. A filter medium of claim 16 wherein said microbiological interception enhancing agent further includes a biologically active metal in direct proximity to the cationic chemical wherein the biologically active metal is caused to precipitate with at least a portion of the counter ion associated with the cationic chemical.

20. A filter medium of claim 19 wherein the biologically active metal comprises silver, copper, zinc, cadmium, mercury, antimony, gold, aluminum, platinum, palladium, or combinations thereof.

21. A filter medium of claim 16 wherein the flow of a fluid through said filter medium decreases in response to an amount of polyanionic acids present in the influent.

22. A filter medium of claim 21 wherein said filter medium retains enhanced interception of microbiological contaminants.

* * * * *